United States Patent [19]

Ohtsuki et al.

[11] Patent Number: 5,326,753
[45] Date of Patent: Jul. 5, 1994

[54] FREEZE-DRIED COMPOSITION CONTAINING A 2-DIMETHYLAMINO ETOPOSIDE DERIVATIVE

[75] Inventors: Kazuo Ohtsuki, Tokyo; Taka'aki Ohkuma, Yono, both of Japan

[73] Assignee: Nippon Kayaku Kabushiki Kaisha, Tokyo, Japan

[21] Appl. No.: 887,589

[22] Filed: May 20, 1992

Related U.S. Application Data

[63] Continuation of Ser. No. 636,676, Jan. 2, 1991, abandoned.

[30] Foreign Application Priority Data

Jan. 19, 1990 [JP] Japan .................... 2-008153

[51] Int. Cl.$^5$ .................................... A61K 31/70
[52] U.S. Cl. ............................ 514/33; 514/35; 536/17.2; 536/18.1
[58] Field of Search ............ 536/18.1; 514/23, 27, 514/33, 35; 23/294 R; 424/489

[56] References Cited

U.S. PATENT DOCUMENTS

| | | | |
|---|---|---|---|
| 4,713,246 | 12/1987 | Begum et al. | 536/18.1 |
| 4,716,221 | 12/1987 | Umezawa et al. | 536/17.2 |
| 4,757,138 | 7/1988 | Fujii et al. | 536/18.1 |
| 4,772,589 | 9/1988 | Kaplan et al. | 536/18.1 |
| 4,853,467 | 8/1989 | Vyas et al. | 536/18.1 |
| 4,927,638 | 5/1990 | Bykadi et al. | 536/18.1 |
| 4,935,504 | 6/1990 | Saulnier et al. | 536/18.1 |
| 4,997,923 | 3/1991 | Izawa et al. | 536/17.2 |

FOREIGN PATENT DOCUMENTS

| | | | |
|---|---|---|---|
| 0196618 | 10/1986 | European Pat. Off. | 536/18.1 |
| 0369369 | 5/1990 | European Pat. Off. | 536/18.1 |
| 0108416 | 11/1958 | Pakistan | 536/18.1 |
| 1205965 | 9/1970 | United Kingdom | 536/18.1 |
| 1205966 | 9/1970 | United Kingdom | 536/18.1 |

OTHER PUBLICATIONS

Osol ed., *Remington's Pharmaceutical Sciences*, 16th Ed., Mack Publishing Co., Easton, Pa. 1980, pp. 1483–1484.
Ludwig et al; "Chemical and Biological Stability of Anticancer Drugs Used in a Human Tumor Clonogenic Assay," *Cancer Chemother. Pharmacol.* 12:142–145 (1984); *Chem. Abstr.*, 101, p. 345, Abstr. No. 116635u (1984).
Sato et al., "Antitumor Etoposide Injection" (Jp SN 60/239,415); *Chem. Abstr.*, 104, p. 449, Abstr. No. 95509a (1986); only Abstract provided.
Hamon et al., "Study on the Stability in Dilute Solutions Destined for Perfusion of Two Antimitotics Derived from Podophyllotoxin: Etoposide (VP16) and Teniposide (VN26)," *S.T.P. Pharma.*, 3(1), 33–40 (1987); *Chem. Abstr.*, 107, p. 378, Abstr. No. 83767g (1987); only Abstract provided.
Tanaka et al., "Stability of Etoposide," *Kagaku Ryoho no Ryoiki*, 3(9), 1459–1467 (1987); *Chem. Abstr.*, 107, p. 357, Abstr. No. 223147g (1987); only Abstract provided.
Grant et al. eds., *Grant & Hackh's Chemical Dictionary*, McGraw-Hill Book Company, New York, 1987, p. 346.
Seargeant et al., "In Vitro Stability and Compatibility of Daunorubicin, Cytarabine and Etoposide," *Cancer Treatment Repts.*, 71(12):1189–1192; *Chem. Abstr.*, 108, p. 327, Abstr. No. 26897w (1988).
Shah et al; "Preformulation Study of Etoposide: Identification of Physicochemical Characteristics Responsible for the Low and Erratic Oral Bioavailability of Etoposide," *Pharmaceutical Res.*, 6(5):408–412; *Chem. Abstr.*, 111, p. 385, Abstr. No. 83960x (1989).
Stewart et al; "Stability of Cisplatin and Epotoside in Intravenous Admixture," *Am. J. Hospit. Pharm.*, 46:1400–1404 (1989); *Chem. Abstr.*, 111, p. 388, Abstr. No. 140313q (1989).
Aoki et al., "Antitumor Formulations Containing Etoposide," EPO Appl. 401,695; *Chem. Abstr.*, 111, p. 388, Abstr. No. 150207j (1991); only Abstract provided.
Izawa et al; Chemical Abstracts 114:43481x (1991).

*Primary Examiner*—John W. Collins
*Assistant Examiner*—L. Eric Crane
*Attorney, Agent, or Firm*—Nields & Lemack

[57] ABSTRACT

The present invention relates to a freeze-dried preparation comprising (1) about 5 to about 50 W/W% of a non-volatile acid and/or a salt thereof, (2) about 10 to about 95 W/W% of 4-O-(2-deoxy-2-dimethylamino-4,6-O-ethylidene-β-D-glucopyranosyl)-4'-demethyl-4-epipodophyllotoxin hydrochloride and (3) 0 to about 85 W/W% of at least one sugar as a stabilizer.

7 Claims, No Drawings

FREEZE-DRIED COMPOSITION CONTAINING A 2-DIMETHYLAMINO ETOPOSIDE DERIVATIVE

This application is a continuation of application Ser. No. 07/636,676 filed Jan. 2, 1991, now abandoned.

BACKGROUND OF THE INVENTION

1. Field of the Invention

The present invention relates to a stabilized freeze-dried preparation of an etoposide derivative which is useful as an antitumor agent.

2. Statement of the Prior Art

4-O-( 2-Deoxy-2-dimethylamino-4,6-O-ethylidene-$\beta$-D-glucopyranosyl)-4'-demethyl-4-epipodophyllotoxin hydrochloride (hereafter abbreviated as etoposide-2-dimethylamino compound) is a derivative of antitumor agent, etoposide. The etoposide-2-dimethylamino compound is excellent in solubility which is a defect of etoposide and exhibits an antitumor activity (cf. U.S. Pat. No. 4,716,221).

However, the etoposide-2-dimethylamino compound is unstable in an aqueous solution, which makes storage over a long period of time difficult.

A pharmaceutical preparation obtained by merely dissolving the etoposide-2-dimethylamino compound in distilled water followed by freeze drying involves a drawback that when the compound is reconstituted with water, pH of its solution increases to cause precipitation of crystals.

SUMMARY OF THE INVENTION

As a result of various studies on preparation formulations for improving reconstitution, the present inventors have found that a freeze-dried preparation of the etoposide-2-dimethylamino compound containing a non-volatile acid and/or a salt thereof has good reconstitution so that no crystallization occurs, also shows good stability during storage and hardly forms decomposition products, and that its stability further increases by adding sugars. The present invention has thus been accomplished.

The present invention relates to a freeze-dried preparation of the etoposide-2-dimethylamino compound. That is, the present invention provides a freeze-dried preparation comprising: (1) about 5 to about 50 W/W% of a non-volatile acid and/or a salt thereof, (2) about 10 to about 95 W/W% of 4-O-(2-deoxy-2-dimethylamino-4,6-O-ethylidene-$\beta$-D-glucopyranosyl)-4'-demethyl-4-epipodophyllotoxin hydrochloride and (3) 0 to about 85 W/W% of at least one sugar as a stabilizer.

DETAILED DESCRIPTION OF THE INVENTION

The etoposide-2-dimethylamino compound used in the present invention is generally used in the form of its hydrochloride, as shown in Japanese Patent Application KOKAI No. 61-227590. The hydrochloride has three kinds of polymorphism in crystalline form, namely, anhydrous crystals (hereafter abbreviated as $\alpha$ crystals) and two kinds of dihydrated crystals (hereafter abbreviated as $\beta$ crystals and $\gamma$ crystals). According to the present invention, any crystalline form is usable.

As the non-volatile acid and a salt thereof which can be used in the present invention, any acid and salts thereof may be used without any particular restriction so long as they are liquid or solid acids at room temperature, have a required buffering effect in a pH range of not less than 3 to less than 5, at which the etoposide-2-dimethylamino compound is relatively stable and has good solubility, are used for medical purpose and are pharmacologically acceptable. Examples of these acids include inorganic acids such as phosphoric acid, sulfuric acid, etc.; oxycarboxylic acids having 6 carbon atoms ($C_6$) such as citric acid, gluconic acid, etc.; dicarboxylic acids having 4 carbon atoms ($C_4$) such as succinic acid, tartaric acid, fumaric acid, maleic acid, etc.; carboxylic acids having 2 carbon atoms ($C_2$) such as aminoacetic acid, etc. Of these acids, phosphoric acid is particularly preferred. As salts of these acids, alkali metal or alkaline earth metal salts such as sodium salts, potassium salts, magnesium salts, etc. may be used but in general, alkali metal salts are preferred. These acids and/or salts thereof may be used in combination of two or more. The amount of these acids and/or their salts added to the preparation depends on buffering effects of these acids and/or their salts but ranges generally from about 0.1 to about 5 parts by weight, preferably about 0.1 to about 4 parts by weight, more preferably about 0.2 to about 3 parts by weight, based on 1 part by weight of the etoposide-2-dimethylamino compound. A pH value of the preparation in accordance with the present invention is not less than about 3 to less than about 5, preferably not less than about 3.0 to less than about 4.5, as a pH value of reconstituted solution.

The preparation of the present invention may further contain a sugar and the like, if necessary and desired. Examples of the sugar include sugar alcohols having 5 to 6 carbon atoms such as mannitol, sorbitol, xyiitol, inositol, etc.; disaccharides such as lactose, maltose, sucrose, etc. Of these sugars, lactose is preferred though there is no particular restriction. Using the sugar, stability of the etoposide-2-dimethylamino compound during storage is improved. The amount of the sugar is 0 to 30 parts by weight, preferably about 0.1 to about 10 parts by weight, based on 1 part by weight of the etoposide-2-dimethylamino compound. In view of making the compound into pharmaceutical preparations, the amount of about 0.1 to about 4 parts by weight is preferred.

In the freeze-dried preparation of the present invention, the etoposide-2-dimethylamino compound is contained in an amount of about 10 to about 95% (W/W: hereafter the same unless otherwise indicated), preferably about 15 to about 80%, more preferably about 30 to about 50%; the non-volatile acid and/or its salts are contained in an amount of about 5 to about 50%, preferably about 15 to about 35%, more preferably about 20 to about 30%; and the sugar is contained in an amount of about 0 to about 85%, preferably about 0 to about 70%, more preferably about 30 to about 50%; based on the total weight of the composition.

The freeze-dried preparation of the present invention can be prepared, for example, as follows. That is, the etoposide-2-dimethylamino compound and the non-volatile acid and/or its salts and if necessary and desired, the sugar are dissolved in water for injection and, if necessary, pH is adjusted to about 3 to about 5, preferably about 3.0 to about 4.5, with sodium hydroxide, etc. to obtain an aqueous solution. Where the non-volatile acid salt is used, the etoposide-2-dimethylamino compound might not be dissolved depending on its pH. In this case, the non-volatile acid is used and pH is reduced to somewhat below 3 thereby to dissolve the etoposide-2-dimethylamino compound. For example, a preferred composition of the aqueous solution comprises about 5 to about 15 mg/ml of the etoposide-2-dimethylamino compound, about 1 to about 10 mg/ml of the non-volatile acid and/or its salt and 0 to about 50 mg/ml of the sugar.

The thus obtained aqueous solution is frozen at a temperature of −5° to −60° C. and water is then sublimated under reduced pressure at a degree of vacuum of 0.01 to 200 Pa. to give the freeze-dried preparation of the present invention.

The freeze-dried preparation thus obtained is generally re-dissolved by adding dissolving liquid such as water for injection to the preparation and the resulting solution is used as an injection. In this case, it is preferred that a pH value of the dissolving liquid be in a range of about 3 to about 5.

DESCRIPTION OF THE PREFERRED EMBODIMENT

Hereafter the present invention is explained with reference to the examples and test example but is not deemed to be limited thereto.

Example 1

α Crystals were dissolved in 50 mM phosphate buffer obtained by mixing 50 mM phosphoric acid aqueous solution and 50 mM sodium dihydrogenphosphate aqueous solution to render its pH to 3.0, so that its concentration became 10 mg/ml. And then pH of the resulting solution was adjusted to 3.0 with 1 N sodium hydroxide solution. The solution was dispensed into vials at a rate of 1 ml/vial and freeze-dried to give Composition 1 (containing about 63% of the etoposide-2-dimethylamino compound and about 37% of phosphoric acid and its sodium salt) of the present invention.

Example 2

α Crystals and mannitol were dissolved in 50 mM phosphate buffer, pH of which was rendered 3.0 as in Example 1, so that their concentrations became 10 mg/ml and 40 mg/ml, respectively. And then pH of the resulting solution was adjusted to 3.0 with 1 N sodium hydroxide solution. The solution was freeze-dried in the same manner as in Example 1 to give Composition 2 (containing about 18% of the etoposide-2-dimethylamino compound, about 11% of phosphoric acid and its sodium salt and about 71% of mannitol) of the present invention.

Example 3

α Crystals and inositol were dissolved in 50 mM phosphate buffer, pH of which was rendered 3.0 as in Example 1, so that their concentrations became 10 mg/ml and 40 mg/ml, respectively. And then pH of the resulting solution was adjusted to 3.0 with 1 N sodium hydroxide solution. The solution was freeze-dried in the same manner as in Example 1 to give Composition 3 (containing about 18% of the etoposide-2-dimethylamino compound, about 11% of phosphoric acid and its sodium salt and about 71% of inositol) of the present invention.

Example 4

α Crystals and lactose were dissolved in 50 mM phosphate buffer, pH of which was rendered 3.0 as in Example 1, so that their concentrations became 10 mg/ml and 40 mg/ml, respectively. And then pH of the resulting solution was adjusted to 3.0 with 1 N sodium hydroxide solution. The solution was freeze-dried in the same manner as in Example 1 to give Composition 4 (containing about 18% of the etoposide-2-dimethylamino compound, about 11% of phosphoric acid and its sodium salt and about 71% of lactose) of the present invention.

Example 5

α Crystals and maltose were dissolved in 50 mM phosphate buffer, pH of which was rendered 3.0 as in Example 1, so that their concentrations became 10 mg/ml and 40 mg/ml respectively. And then pH of the resulting solution was adjusted to 3.0 with 1 N sodium hydroxide solution. The solution was freeze-dried in the same manner as in Example 1 to give Composition 5 (containing about 18% of the etoposide-2-dimethylamino compound, about 11% of phosphoric acid and its sodium salt and about 71% of maltose) of the present invention.

Example 6

α Crystals and sucrose were dissolved in 50 mM phosphate buffer, pH of which was rendered 3.0 as in Example 1, so that their concentrations become 10 mg/ml and 40 mg/ml, respectively. And then pH of the resulting solution was adjusted to 3.0 with 1 N sodium hydroxide solution. The solution was freeze-dried in the same manner as in Example 1 to give Composition 6 (containing about 18% of the etoposide-2-dimethylamino compound, about 11% of phosphoric acid and its sodium salt and about 71% of sucrose) of the present invention.

Example 7

α Crystals were dissolved in 50 mM citrate buffer obtained by mixing 50 mM citric acid aqueous solution and 50 mM trisodium citrate aqueous solution to render its pH to 3.0, so that its concentration became 10 mg/ml. And then pH of the resulting solution was adjusted to 3.0 with 50 mM trisodium citrate aqueous solution. The solution was freeze-dried in the same manner as in Example 1 to give Composition 7 (containing about 49% of the etoposide-2-dimethylamino compound and about 51% of phosphoric acid and its sodium salt) of the present invention.

Example 8

α Crystals and mannitol were dissolved in 50 mM citrate buffer, pH of which was rendered 3.0 as in Example 7, so that their concentrations became 10 mg/ml and 40 mg/ml, respectively. And then pH of the resulting solution was adjusted to 3.0 with 50 mM trisodium citrate aqueous solution. The solution was freeze-dried in the same manner as in Example 1 to give Composition 8 (containing about 17% of the etoposide-2-dimethylamino compound, about 17% of citric acid and its sodium salt and about 66% of mannitol) of the present invention.

Example 9

β Crystals were dissolved in 50 mM phosphate buffer, pH of which was rendered 3.0 as in Example 1, so that its concentration became 10mg/ml. And then pH of the resulting solution was adjusted to 3.0 with 1 N sodium hydroxide solution. The solution was dispensed into vials at a rate of 2 ml/vial and freeze-dried, to give Composition 9 (containing about 63% of the etoposide-2-dimethylamino compound and about 37% of phosphoric acid and its sodium salt) of the present invention.

Example 10

β Crystals were dissolved in 50 mM phosphate buffer, which is the same one as used in Example 1, so that its concentration became 10 mg/ml. And then pH of the resulting solution was adjusted to 4.0 with 1 N sodium hydroxide solution. The solution was freeze-dried in the same manner as in Example 9 to give Composition 10 (containing about 63% of the etoposide-2-dimethylamino compound and about 37% of phosphoric acid and its sodium salt) of the present invention.

Example 11

β Crystals were dissolved in 25 mM phosphate buffer obtained by mixing 25 mM phosphoric acid aqueous solution and 25 mM sodium dihydrogenphosphate aqueous solution to render its pH to 3.0, so that ,its concentration became 10 mg/ml, as in Example 9. And then pH of the resulting solution was adjusted to 3.5 with 1 N sodium hydroxide solution. The solution was freeze-dried in the same manner as in Example 9 to give Composition 11 (containing about 77% of the etoposide-2-dimethylamino compound and about 23% of phosphoric acid and its sodium salt) of the present invention.

Example 12

β Crystals and mannitol were dissolved in 50 mM phosphate buffer as in Exampel 9, so that their concentrations become 10 mg/ml and 4 mg/ml, respectively. And then pH of the resulting solution was adjusted to 3.5 with 1 N sodium hydroxide solution. The solution was freeze-dried in the same manner as in Example 9 to give Composition 12 (containing about 50% of the etoposide-2-dimethylamino compound, about 30% of phosphoric acid and its sodium salt and about 20% of mannitol) of the present invention.

Example 13

β Crystals and lactose were dissolved in 50 mM phosphate buffer as in Example 9, so that their concentrations became 10 mg/ml. And then pH of the resulting solution was adjusted to 3.0 with 1 N sodium hydroxide solution. The solution was freeze-dried in the same manner as in Example 9 to give Composition 13 (containing about 37% of the etoposide-2-dimethylamino compound, about 26% of phosphoric acid and its sodium salt and about 37% of lactose) of the present invention.

Example 14

β Crystals and sorbitol were dissolved in 25 mM phosphate buffer as in Example 9, so that their concentrations became 10 mg/ml. And then pH of the resulting solution was adjusted to 3.5 with 1 N sodium hydroxide solution. The solution was freeze-dried in the same manner as in Example 9 to give Composition 14 (containing about 42% of the etoposide-2-dimethylamino compound, about 17% of phosphoric acid and its sodium salt and about 41% of sorbitol) of the present invention.

Example 15

β Crystals and xylitol were dissolved in 25 mM phosphate buffer as in Example 9, so that their concentrations became 10 mg/ml. And then pH of the resulting solution was adjusted to 3.5 with 1 N sodium hydroxide solution. The solution was freeze-dried in the same manner as in Example 9 to give Composition 15 (containing about 42% of the etoposide-2-dimethylamino compound, about 17% of phosphoric acid and its sodium salt and about 41% of xylitol) of the present invention.

Comparative Example 1

α Crystals were dissolved in water so that its concentration became 10 mg/ml. And then pH of the resulting solution was adjusted to 3.0 with 1 N hydrochloric acid. The solution was freeze-dried in the same manner as in Example 1 to give Comparative Composition 1.

Comparative Example 2

α Crystals and lactose were dissolved in water, so that their concentrations became 10 mg/ml. And then the resulting solution was freeze-dried in the same manner as in Example 1 to give Comparative Composition 2 (containing about 50% of the etoposide-2-dimethylamino compound and about 50% of lactose).

Next, the following test example was carried out to demonstrate that the freeze-dried preparation of the present invention comprising the etoposide-2-dimethylamino compound has an excellent stability during storage and its reconstitution is improved.

Test Example

Compositions 1 through 15 of the present invention, Comparative Composition 1, pH of which was adjusted with a volatile acid followed by freeze-drying, and Comparative Composition 2 which was obtained by adding the sugar alone without adjusting its pH and then freeze-drying, were examined immediately after freeze-drying and after storage under severe conditions of 60° to 65° C. for one week, in terms of appearance, reconstitution, pH and residual content of the etoposide-2-dimethylamino compound. The residual content was determined by liquid chromatography, in which the total amount of the etoposide-2-dimethylamino compound and the decomposition products was made 100. After adding 1 ml of distilled water to each vial of Examples 1 through 8 and Comparative Examples 1 and 2, and adding 2 ml of distilled water in Examples 9 through 15 to have the etoposide-2-dimethylamino compound in a concentration of 10 mg/ml, the reconstitution was observed in terms of a degree of dissolving the dry powders and presence or absence of crystallization after dissolution. As the result, crystals were precipitated in Comparative Examples 1 and 2 at pH of 5 or more, when the compositions were reconstituted. Thus, the Comparative Compositions were both unsuited for preparations for injection.

Turning to the present invention Compositions 1 through 15 showed good re-solubility as presented in Table; no crystallization occurred and pH change was relatively small. As the result, storage stability was also good. By adding the sugar, the residual content was further improved.

TABLE

| Sample | Appearance | Reconstitution | pH | Residual content (%) |
| --- | --- | --- | --- | --- |
| Example 1 | good | good | 3.3 | 89.8 |
| Example 2 | good | good | 3.3 | 93.4 |
| Example 3 | good | good | 3.3 | 99.1 |
| Example 4 | good | good | 3.3 | 99.3 |
| Example 5 | good | good | 3.3 | 99.1 |
| Example 6 | good | good | 3.3 | 98.4 |

TABLE -continued

| Sample | Appearance | Reconstitution | pH | Residual content (%) |
|---|---|---|---|---|
| Example 7 | good | good | 3.2 | 88.5 |
| Example 8 | good | good | 3.2 | 93.2 |
| Example 9 | good | good | 3.2 | 90.4 |
| Example 10 | good | good | 4.4 | 98.9 |
| Example 11 | good | good | 4.1 | 99.0 |
| Example 12 | good | good | 3.7 | 99.1 |
| Example 13 | good | good | 3.0 | 99.4 |
| Example 14 | good | good | 3.6 | 98.2 |
| Example 15 | good | good | 3.7 | 98.4 |
| Comparative Example 1 | good | Crystallization | >5.0 | — |
| Comparative Example 2 | good | Crystallization | >5.0 | — |

According to the present invention, the preparation of the etoposide-2-dimethylamino compound which has good reconstitution and stable pH and residual content can be provided as described above.

We claim:

1. A freeze-dried preparation consisting essentially of (1) about 5 to about 50 W/W% of a combination of a non-volatile acid and a pharmaceutically acceptable salt thereof selected from the group consisting of phosphoric acid with its pharmaceutically acceptable salt, an oxycarboxylic acid having 6 carbon atoms with its pharmaceutically acceptable salt, a dicarboxylic acid having 4 carbon atoms with its pharmaceutically acceptable salt, and an aminoacetic acid with its pharmaceutically acceptable salt, (2) about 15 to about 80 W/W% of 4-O-(2-deoxy-2-dimethylamino-4,6-O-ethylidene-$\beta$-D-glucopyranosyl)-4'-demethyl-4-epipodophyllotoxin hydrochloride and (3) at least one sugar as a stabilizer, such that said freeze-dried preparation, upon reconstitution with water, does not crystallize and has a pH not less than about 3 but less than about 5.

2. A freeze-dried preparation according to claim 1, wherein said non-volatile acid and a salt thereof are phosphoric acid and its alkali metal salt or citric acid and its alkali metal salt.

3. A freeze-dried preparation according to claim 1, wherein said sugar is a sugar alcohol having 5 to 6 carbon atoms or a disaccharide.

4. A freeze-dried preparation according to claim 1, wherein said sugar is selected from the group consisting of lactose, maltose, sucrose and mannitol.

5. A freeze-dried preparation consisting essentially of (1) about 15 to about 35 W/W% of phosphoric acid and an alkali metal salt thereof, (2) about 15 to about 80 W/W% of 4-O-(2-deoxy-2-dimethylamino-4,6-O-ethylidene-$\beta$-D-glucopyranosyl)-4'-demethyl-4-epipodophyllotoxin hydrochloride and (3) 0 to about 70 W/W% of lactose as a stabilizer, such that said freeze-dried preparation, upon reconstitution with water, does not crystallize and has a pH not less than about 3 but less than about 5.

6. A freeze-dried preparation consisting essentially of (1) about 20 to about 30 W/W% of phosphoric acid and an alkali metal salt thereof, (2) about 30 to about 50 W/W% of 4-O-(2-deoxy-2-dimethylamino-4,6-O-ethylidene-$\beta$-D-glucopyranosyl)-4'-demethyl-4-epipodophyllotoxin hydrochloride and (3) about 30 to about 50 W/W% of lactose as a stabilizer, such that said freeze-dried preparation, upon reconstitution with water, does not crystallize and has a pH not less than about 3 but less than about 5.

7. A freeze-dried preparation consisting essentially of (1) about 0.1 to about 5 parts by weight of a combination of a non-volatile acid and a pharmaceutically acceptable salt thereof selected from the group consisting of phosphoric acid with its pharmaceutically acceptable salt, an oxycarboxylic acid having 6 carbon atoms with its pharmaceutically acceptable salt, a dicarboxylic acid having 4 carbon atoms with its pharmaceutically acceptable salt, and an aminoacetic acid with its pharmaceutically acceptable salt, (2) 1 part by weight of 4-O-(2-deoxy-2-dimethylamino-4,6-O-ethylidene-$\beta$-D-glucopyranosyl)-4'-demethyl-4-epipodophyllotoxinhydrochloride and (3) about 0.1 to about 10 parts by weight of at least one sugar as a stabilizer, such that said freeze-dried preparation, upon reconstitution with water, does not crystallize and has a pH not less than about 3 but less than about 5.

* * * * *